United States Patent [19]
Hassan et al.

[11] Patent Number: 5,844,287
[45] Date of Patent: Dec. 1, 1998

[54] MONOLITHIC SENSOR OF FINGERPRINTS

[75] Inventors: Salman Abou Hassan, Caen; Marie-Josèphe Revillet, Verson, both of France

[73] Assignees: France Telecom, Paris; La Poste, Bulogne-Billancourt Cedex, both of France

[21] Appl. No.: 728,329

[22] Filed: Oct. 10, 1996

[30] Foreign Application Priority Data

Oct. 17, 1995 [FR] France .................................. 95 12168

[51] Int. Cl.⁶ .................................................. H01L 29/82
[52] U.S. Cl. ........................ 257/419; 257/415; 257/418; 257/108; 438/53
[58] Field of Search ................................ 257/108, 418, 257/419, 415; 437/228, 233; 438/53

[56] References Cited

U.S. PATENT DOCUMENTS

| | | | |
|---|---|---|---|
| 4,394,773 | 7/1983 | Ruell ........................................... | 382/4 |
| 4,577,345 | 3/1986 | Abramov .................................... | 382/4 |
| 4,965,415 | 10/1990 | Young et al. .......................... | 200/83 N |
| 5,242,863 | 9/1993 | Xiang-Zheng et al. ................ | 437/228 |
| 5,373,181 | 12/1994 | Scheiter et al. ......................... | 257/415 |
| 5,438,875 | 8/1995 | Fung et al. ............................... | 73/721 |
| 5,471,086 | 11/1995 | Ipposhi et al. .......................... | 257/417 |
| 5,637,905 | 6/1997 | Carr et al. ................................ | 257/418 |

FOREIGN PATENT DOCUMENTS

| | | |
|---|---|---|
| A-0457398 | 11/1991 | European Pat. Off. . |
| A-0566336 | 10/1993 | European Pat. Off. . |
| A-2674051 | 9/1992 | France . |

*Primary Examiner*—Mahshid D. Saadat
*Assistant Examiner*—Allan R. Wilson
*Attorney, Agent, or Firm*—Nilles & Nilles, S.C.

[57] ABSTRACT

An electronic fingerprint sensor works by the detection of pressure, the ridge lines of the finger exerting a greater pressure than the valleys. The sensor has a matrix of pressure microsensors and electronic control and signal-processing circuits. It is made in an entirely monolithic form, according to techniques for the making of electronic circuits (deposition of thin layers, photo-etching, doping and thermal processing), both for the pressure detection part and for the signal-processing and control part. The matrix-type pressure sensor uses either piezoelectric resistors lying on an insulator layer stretched above a cavity or a variable capacitor or a microcontactor.

19 Claims, 4 Drawing Sheets

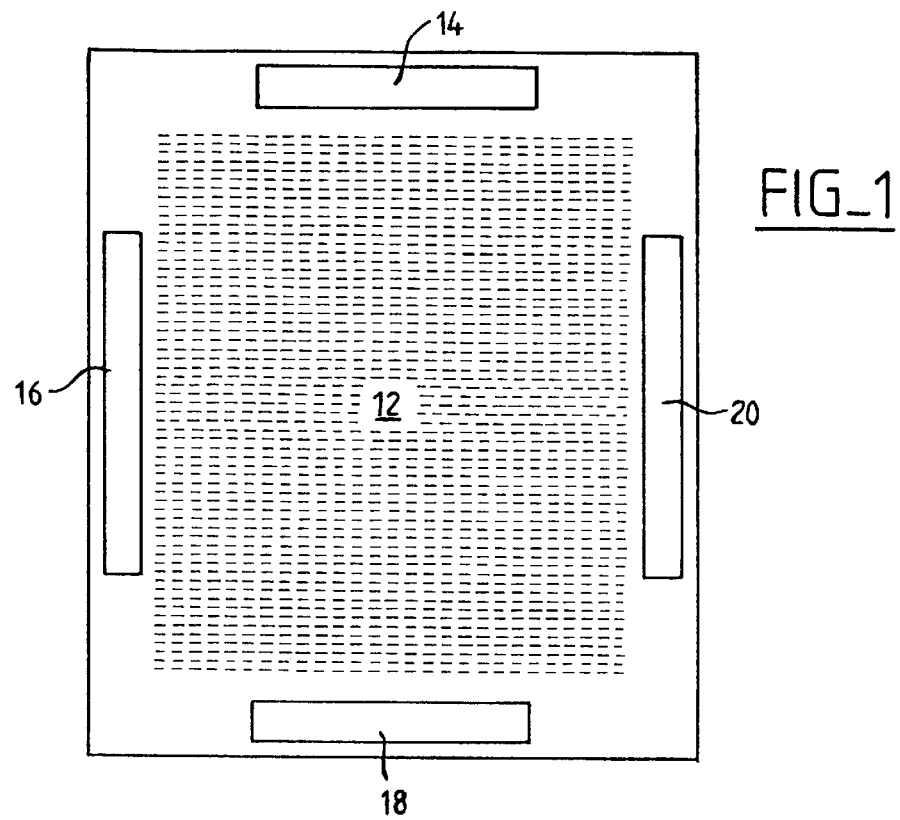
FIG_1
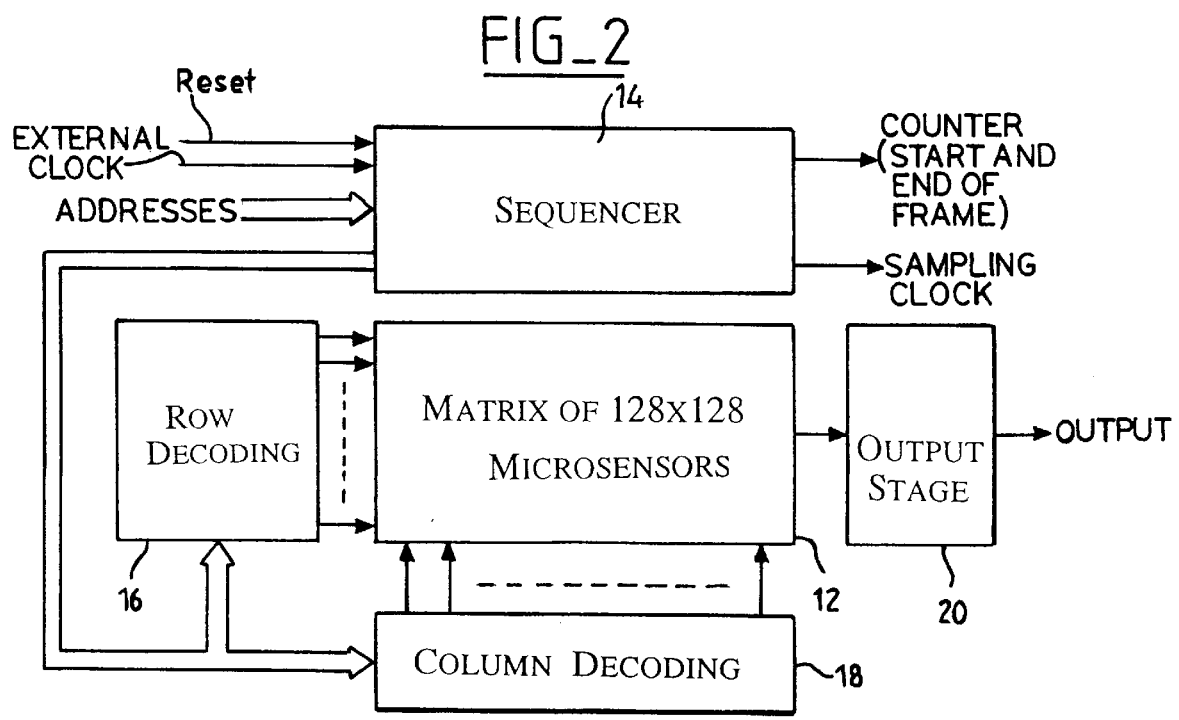
FIG_2

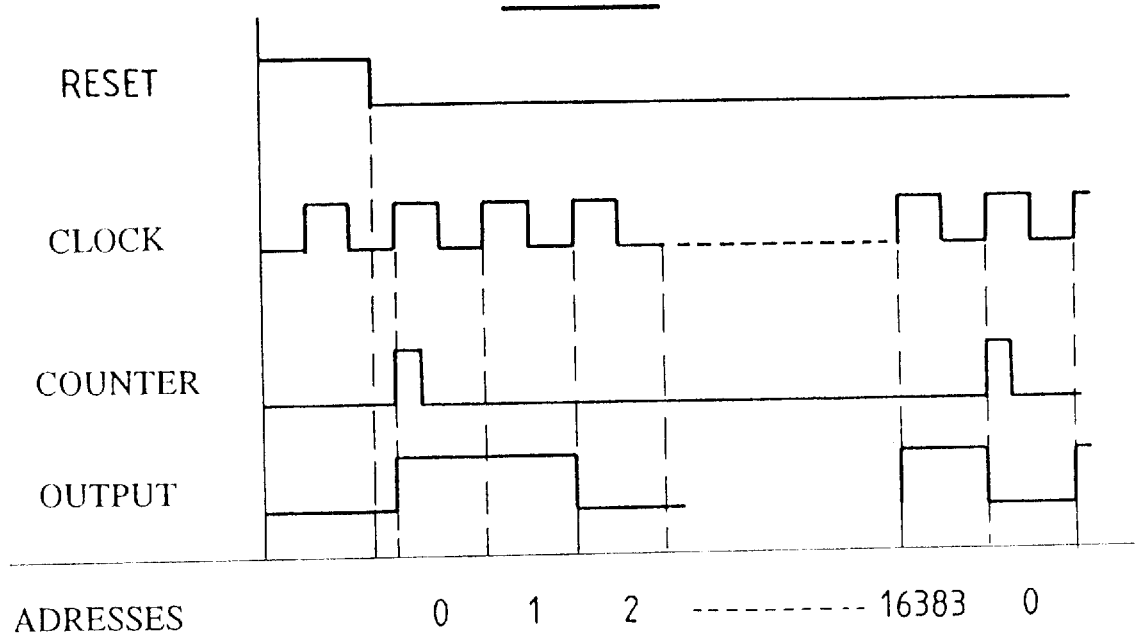
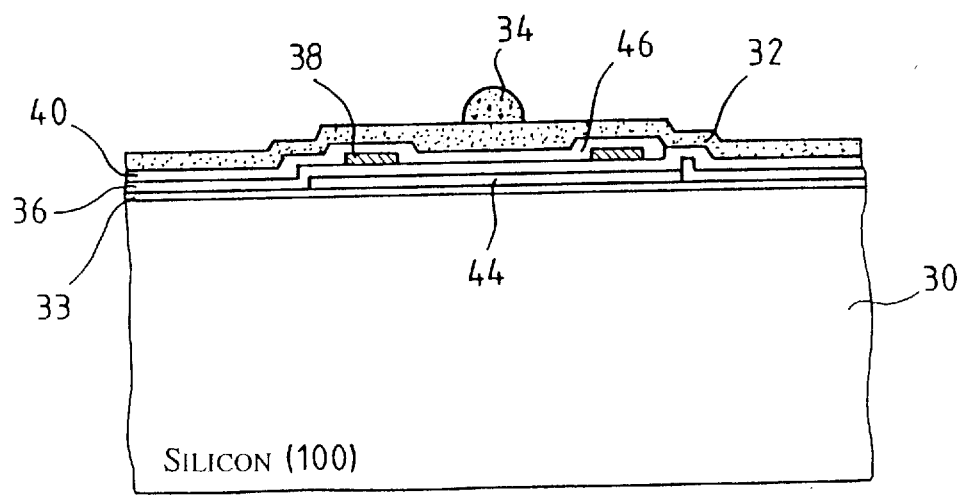

MONOLITHIC SENSOR OF FINGERPRINTS

BACKGROUND OF THE INVENTION

1. Field of the Invention

The invention relates to the field of the authentication of individuals through the recognition of their fingerprints.

It is known that fingerprints have been used for a long time because of the practically one-to-one relationship that exists between a fingerprint and a individual, i.e. because in principle two different individuals will have different fingerprints.

2. Description of the Prior Art

The conventional method of using this particular aspect of nature is an ink-based printing method. It consists in pressing the finger on an inked surface and then placing this finger on a white paper surface. The ridge lines press on the white surface to a greater extent than do the valleys. The ink of the ridge lines is better distributed on the paper than the ink of the valleys, and a pattern of the ridge lines appears clearly on the white surface.

This conventional method is not pleasant for the individual who has to ink his finger and then clean it; and it does not directly enable automatic processing for image recognition.

Other methods have been thought of, based on optical and electronic systems, designed firstly to take a picture of the fingerprint and secondly to process this fingerprint by computer.

These methods generally entail major equipment and high costs. The optical methods also suffer the handicap of sensitivity to dirt, which affects the quality of the signal and appreciably lowers the reliability of the system of acquisition and identification.

They are inconvenient to use because they require regular maintenance.

There are other systems of taking fingerprints based on the conversion of the fingerprint into an electrical signal which, after being shaped, can be processed by a computer.

The U.S. Pat. No. 4,577,345 describes a method and device for the taking and identification of fingerprints using an array of contact pads on an integrated circuit chip.

Localized electrical contacts may be set up at each point of the array by simple pressure above this point.

The ridge lines of the fingerprints exert a higher pressure than the valleys and consequently, the pressure of the finger may set up a pattern of electrical contacts corresponding to the ridge lines while the valleys define a pattern without contact pads.

The pattern thus drawn may be detected by an array of transistors connected to the possible contact pads.

In practice, a flexible conductive membrane is stretched above the upper surface of the integrated circuit and bonded to the entire periphery of this circuit. It is this membrane that sets up the electrical contacts at each point of the network as a function of the pattern of pressure exerted by the finger.

This type of approach has several drawbacks, including especially the fact that the process of manufacture is heterogeneous since integrated circuit technologies and other technologies are mixed with one another.

The assembling of the membrane especially is an operation that does not belong to the technology of integrated circuits and is difficult to perform. The cost of production therefore remains high.

Furthermore, the use of a membrane embrittles the fingerprint-taking system. The membrane may easily break after a number of uses. Finally, presently used membranes do not have the fineness of grain required for sufficient resolution enabling adequate processing of the picture of the fingerprint.

An object of the invention is a fingerprint sensor that does not have the drawbacks encountered in the prior art.

According to the invention, there is proposed a fingerprint sensor comprising a pressure detection means sensitive to the pattern of the fingerprint and electronic circuits that are coupled to this detection means and enable the furnishing of the electrical signals representing this pattern. This sensor is monolithic (without any attached parts) and made entirely according to a technology for the manufacture of electronic integrated circuits both for the pressure detecting means and for the electronic circuits coupled to this means.

The integrated circuit manufacturing technologies are techniques of thin-layer deposition, photolithography and the dry or wet etching of these layers, possible doping by impurities and various types of thermal treatment. They are performed in batches on wafers comprising several identical integrated circuits.

The fingerprint sensor therefore consists of a single integrated circuit that combines all the functions necessary to convert the relief features of the skin of the finger (ridges and valleys) into electrical signals that are preferably sent out in digital form (sequences of binary signals). There is no membrane attached to the circuit by a method of mechanical fastening. All the elements of the sensor are made by the deposition and etching of thin layers.

The component according to the invention is preferably made by a standard CMOS process using the techniques of micro-machining that are presently well mastered. There is no need for any assembling of separately made parts.

The fingerprint sensor will be the input point of a system of identification and/or authentication of fingerprints, installed in a personal computer (PC) or at a workstation connected to a central computer.

The system leads to a reconstitution of the image of the fingerprint by using the coordinates (X, Y) of each point of the pattern picked up by the pressure detection means.

The computer provides the sensor with control signals such as a clock, a reset signal or the like. Since the sensor is in principle a matrix sensor, the microcomputer can carry out point-by-point checks on the access to the different cells of the matrix. The cells of the matrix are pressure microsensors, the entire set of microsensors giving a total matrix image of the pattern of pressures resulting from the application of the finger to the sensor.

The computer receives a measurement signal from the sensor, representing the pressure at each cell, and correlates the signals with counting signals representing the position of this point in an image frame.

The image set up may be processed by a specialized algorithm and compared with other images stored in a database.

SUMMARY OF THE INVENTION

An object of the invention therefore is a fingerprint sensor comprising a matrix of pressure microsensors (12) sensitive to the pattern of a fingerprint, the sensor being made on a substrate according to an integrated circuit manufacturing technology, wherein chiefly each microsensor of the matrix comprises a cavity (44) closed by a diaphragm (46) consisting of an insulator material to bear conductive elements of the microsensor and enable their deformation under the effect of a pressure.

An object of the invention is also a method for the making of a fingerprint sensor comprising a matrix of pressure detection microsensors (12) sensitive to the pattern of a fingerprint and electronic circuits (14, 16, 18, 20) that are coupled to these detection means and are used to provide electrical signals representing this pattern, the sensor being made entirely by means of an integrated circuit manufacturing technology both for the matrix of microsensors and for the electronic circuits coupled to the matrix, wherein this method comprises the following steps:

the deposition of a layer of polycrystalline silicon (35) on the substrate (30);

the photoetching of this layer except in the positions of each microsensor;

the deposition of an insulator layer (36) on the entire surface of the substrate;

the deposition of a second layer of polycrystalline silicon (38);

the etching of this second layer of polycrystalline silicon (38) to make bridges of piezoelectric resistors each corresponding to a microsensor;

the deposition of a second layer of insulator (40) to protect the resistors;

the corrosion of the first layer of polycrystalline silicon at the unprotected positions thus forming a cavity beneath the piezoelectric resistors so that these resistors are suspended on the insulator layer formed by the layers of silicon nitride (36, 40).

An object of the invention is also a method for the making of a fingerprint sensor comprising a matrix of pressure detection microsensors (12) sensitive to the pattern of a fingerprint and electronic circuits (14, 16, 18, 20) that are coupled to these detection means and are used to provide electrical signals representing this pattern, the sensor being made entirely by means of an integrated circuit manufacturing technology both for the matrix of microsensors and for the electronic circuits coupled to the matrix, wherein this method comprises the following steps:

the deposition of a layer of metal and etching to form a first microcontactor electrode (51);

the deposition of a layer of polycrystalline silicon (35) or of metal;

the photoetching of this layer to obtain a diaphragm with a desired geometry;

the deposition of a layer of insulator material (36) on the entire surface of the substrate;

the deposition of a second layer of metal and etching to form a second microcontactor electrode (52);

the deposition of an insulator layer to protect the electrodes;

the corrosion of the layer of polycrystalline silicon at the unprotected places thus forming a cavity within which the electrodes are face to face.

According to a first embodiment, the pressure microsensors work according to a piezoresistive effect: they are resistors whose value varies with the pressure exerted.

Other physical effects are also envisaged to detect the pressure at each cell of the matrix. According to a second embodiment, each pressure microsensor is constituted by a microcontactor.

According to a third embodiment, each pressure microsensor element is constituted by a variable capacitor.

In the case of piezoelectric resistors, the microsensors are formed by a bridge of piezoelectric resistors deposited on a diaphragm stretched above a cavity. The deformation of the diaphragm, under the effect of the pressure, prompts the deformation of the resistors and therefore a variation of their values.

In the case of microcontactors or variable-capacitance capacitors, the microsensor consists of two distant layers of metal forming either the electrodes of the variable-capacitance capacitor or the terminals of the microcontactor, and a layer of insulator (36) stretched above a cavity, forming a diaphragm, the upper electrode being fixedly joined to this diaphragm.

The sensor according to the present invention provides the following advantages as compared with prior art approaches:

greater precision, improved mechanical behavior, simplified manufacture (for there is no problem of the assembling of a membrane or of piezoelectric material), hence lower costs, insensitivity to temperature as compared with a technology using piezoelectric material, whence greater reliability.

BRIEF DESCRIPTION OF THE DRAWINGS

Other features and advantages of the invention shall appear from the following detailed description, made with reference to the appended figures of which:

FIG. 1 shows a general view of the sensor;

FIG. 2 shows the general electrical configuration of the sensor;

FIG. 3 shows a graph of electrical signals;

FIG. 4 shows a sectional view of the structure of an individual microsensor;

MORE DETAILED DESCRIPTION

Figure 5A:
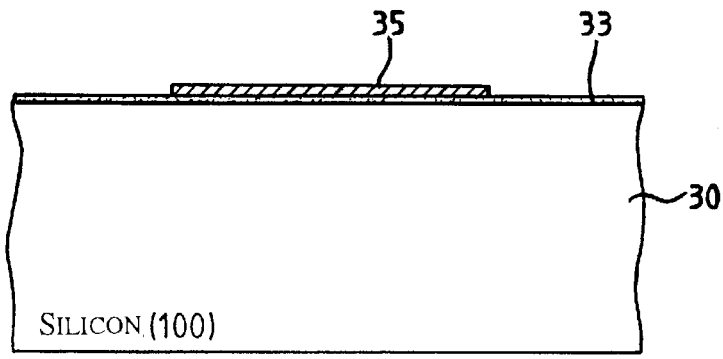
FIGS. 5A–5D show a method for the manufacture of this first structure.

FIG. 1 shows the general constitution of a sensor according to the invention. It essentially has a matrix of 128×128 individual elements which are pressure microsensors arranged in a network of rows and columns.

Each element takes up a square surface area of about 50 micrometers by 50 micrometers or a circle with a diameter of 50 about micrometers.

The pitch of the network is preferably at most 65 micrometers. In other words, the distance between the centers of two adjacent elements is 65 micrometers at the most: the total surface area of the matrix is therefore 8.3×8.3 square millimeters, sufficient to take the central part of a fingerprint which is the zone with the greatest wealth of information. The dimensions given here above correspond to an exemplary embodiment. They give a sufficiently precise definition of the fingerprint and can be made technologically without any particular difficulty.

The microsensors may be made by several techniques using different physical effects for the detection of pressure. The sensors may work on a capacitive effect or a piezoelectric effect, or by means of a simple microcontactor integrated into the monolithic circuit.

Each element may contain a simple electronic circuitry which, by comparison with a threshold, converts the pressure variation into a binary logic level.

In the case of a microsensor with capacitive effect, the circuitry for the detection of pressure variations is therefore more complex and cannot truly be incorporated into each microsensor. Rather, it must be installed on the periphery of the sensor. It is possible, as the case may be, to provide for the association of a memory cell with each microsensor within the matrix.

In the case of a microsensor with microcontactor, the electronic detection circuitry is very simple to make. The binary information is made in the microsensor itself (the switch being open or closed depending on the presence or absence of pressure).

In both cases of microsensors with capacitive effect and piezoelectric effect, it is possible to obtain an analog signal. This possibility enables the performance of more elaborate processing operations on the image of the fingerprint (display in several levels of gray, processing by neural networks, etc.).

The covered zone of microsensors is designated by the reference 12 at the center of the monolithic integrated circuit. The periphery is surrounded with different circuits which are in particular:

a sequencer 14 that ensures the process of the entry of information when the finger is applied. The sequencer has at least one counter (preferably 14 bits), a clock signal generator and an address selector;

a row address decoder 16;

a column address decoder 18;

an output stage 20 comprising electronic circuits for the detection and processing of analog signals, if the individual microsensors do not include this function, and output amplifiers for the transmission, to the output of the sensor, of information elements representing the pattern of pressure detected by the matrix network of microsensors.

FIG. 2 shows the electrical diagram of the fingerprint sensor. The sequencer 14 receives the reset signal, an external clock signal and as the case may be addresses for the point-by-point or row-by-row exploration of the matrix image collected by the microsensors. The image however may be transmitted to the exterior to the integrated circuit by systematic row-by-row scanning similar to a video image scanning: the sequencer then comprises the circuit elements needed to carry out this scanning.

The sequencer transmits row and column addresses to the row and column decoders (16 and 18) enabling point-by-point access to the pressure microsensors of the matrix 12. The electrical signal coming from a microsensor addressed by these decoders is transmitted to an output of the monolithic sensor through the output stage 20.

FIG. 3 shows the output signals of the sensor and the associated control signals. The reset signal (Reset) defines the beginning of a methodical exploration of the matrix.

The clock defines the rate of exploration (for example a clock stroke for each cell of the matrix); the successive addresses are incremented, for example row by row. For a 128×128 matrix, there are 16384 successive addresses to be explored. The frame counter gives a reset pulse to define each new start of transmission of a complete image.

The output signals transmitted, in the case of piezoelectric resistors, are binary signals representing the fact that a threshold of pressure has been exceeded or not exceeded at each cell of the matrix. The signals may be transmitted in series or in parallel in words of 8 bits, 16 bits or more.

In the case of microcontactors or variable-capacitance capacitors, the output signal is an analog signal.

When a fingerprint is being taken, the sensor comes into direct contact with a hostile environment. It therefore needs to be protected. Apart from a passivation layer by which the process for the manufacture of the CMOS circuits is ended, it is possible to deposit a flexible layer (of silicone for example) as a final protective device.

This layer may be used also to improve the function of the transfer of pressure between the finger and the microsensors. In this case, it is possible to make a pad in this layer, formed by an excess thickness at the center of each microsensor, also in order to improve this transfer function.

FIG. 4 shows a sectional view of a structure of this kind with the flexible protection layer 32 deposited on the surface of an integrated circuit substrate 30 in which the pressure microsensors and all the corresponding electronic signal-processing circuitry have been made beforehand.

The layer 32 has, at the center of each microsensor, an excess thickness forming a central pad 34. The excess thickness may be obtained by the successive deposition of two layers, the first layer being uniform and the second one being deposited through a mask demarcating the pads with excess thickness.

The material of the layer 32 is preferably silicone which is both flexible and resistant.

There are several techniques that can be used to make a monolithic sensor comprising microsensors made of micromachined silicon. These techniques are compatible with the making of integrated electronic circuits (preferably in CMOS technology).

The following is a detailed description of an exemplary embodiment pertaining to pressure microsensors using a piezoresistive effect. The method is compatible with a CMOS technology and therefore enables the integration, on one and the same integrated circuit chip, of the microsensors and signal processing and control electronic circuits.

Figure 5B:
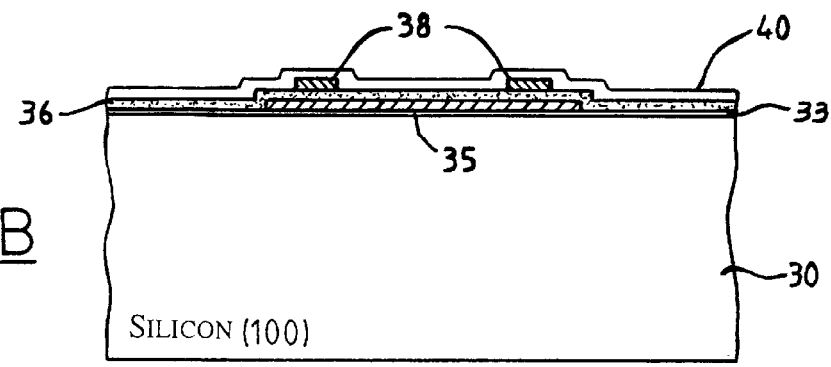
Figure 5C:
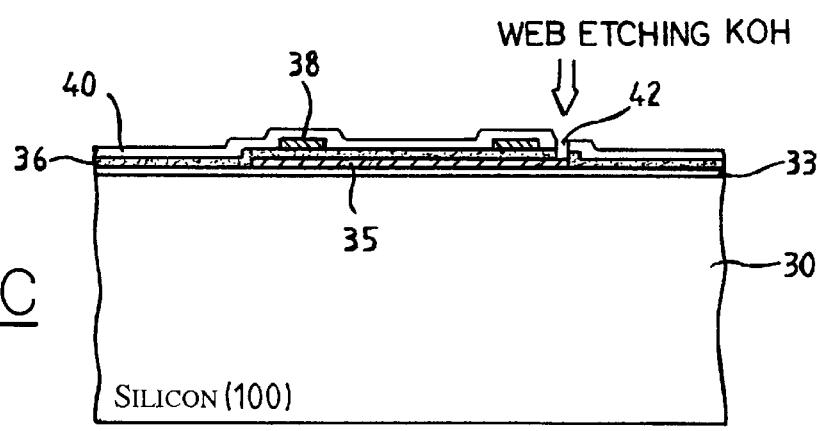
Figure 5D:
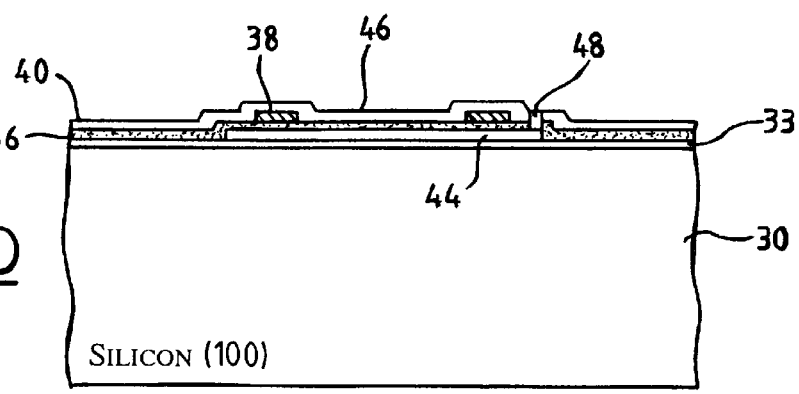

FIGS. 5A–5D show the main steps of manufacture.

On a silicon substrate 30 possibly coated with a fine etching barrier layer 33 (made of silicon nitride), there is deposited a sacrificial or sacrificed layer of polycrystalline silicon 35.

This layer is photoetched to leave a zone of polycrystalline silicon at the position of each microsensor.

Then, a fine layer of silicon nitride 36 is deposited on the entire surface of the substrate, and then a second layer of polycrystalline silicon 38. This second layer is etched to make bridges of piezoelectric resistors (a Wheatstone bridge of four resistors) each corresponding to a pressure microsensor.

One or more resistors of a bridge are deposited above polycrystalline silicon zones of the first layer. Then a second layer of silicon nitride 40 is deposited to protect the resistors.

The next step consists in making holes 42 in the layers of silicon nitride, beside the resistors but above the zones of the first polycrystalline silicon layer 35.

Through these holes, access is obtained to the first polycrystalline silicon layer 35, through the two nitride layers 36 and 40.

A wet etching (KOH) is performed to corrode the polycrystalline silicon wherever it is not protected. The corrosion is achieved through the holes 42 and the totality of the sacrificial layer 35 is removed through these holes. The silicon is protected elsewhere by the nitride layers and by the etching barrier layer 33.

A cavity 44 then remains beneath the piezoelectric resistors which are then suspended over a stretched insulator layer that may undergo deformation when pressure is exerted on them.

The stretched insulator layer is herein constituted by the silicon nitride layers 36 and 40 forming a diaphragm 46 suspended above the cavity 44. The side walls of the cavity are made of silicon nitride. The bottom consists of a thin etching barrier layer 33 lying on the substrate.

When the etching is over, it is possible to redeposit the silicon nitride 48 in order to plug the holes 42 and thus seal the cavities.

The electronic control and processing circuits are formed simultaneously by standard operations of deposition and etching using CMOS technology, some of the above steps being common with steps for the making of CMOS circuits and all the steps being in any case compatible with the making of CMOS circuits on the same substrate.

The flexible protection layer 32 (FIG. 4) made of silicone or a similar material is deposited at the end of the method, after the standard steps of final passivation (deposition of layers of silica or the like) in integrated circuits.

The following is a detailed description of an exemplary embodiment of the pressure microsensors using capacitive effect or using microcontactors. In both cases, the method of manufacture is the same. Only the thickness of the diaphragm changes to enable or not enable the setting up of a contact. One order of magnitude of this thickness is 0.5 µm.

Figure 6A:
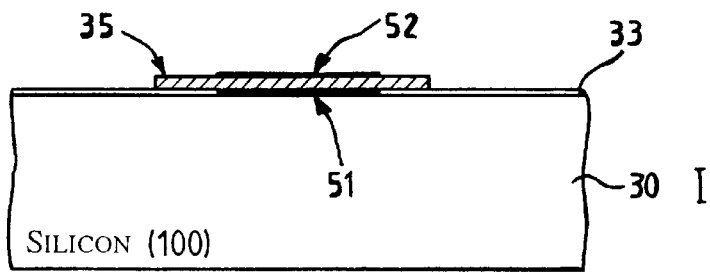
FIGS. 6A–6E show a method for the manufacture of a second structure according to the invention.
Figure 6B:
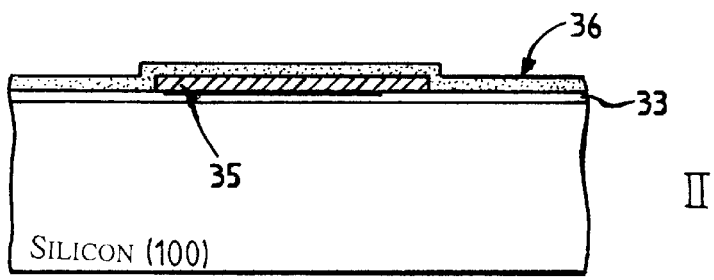
Figure 6C:
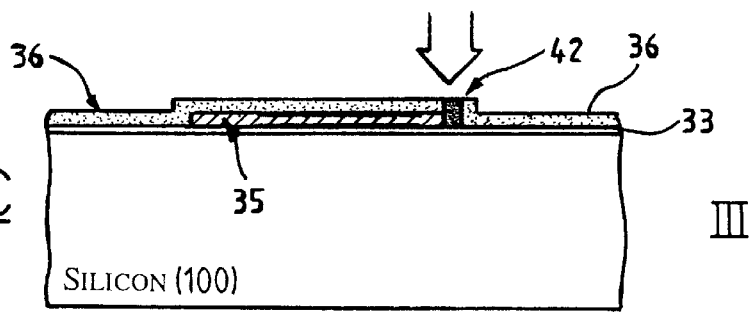
Figure 6D:
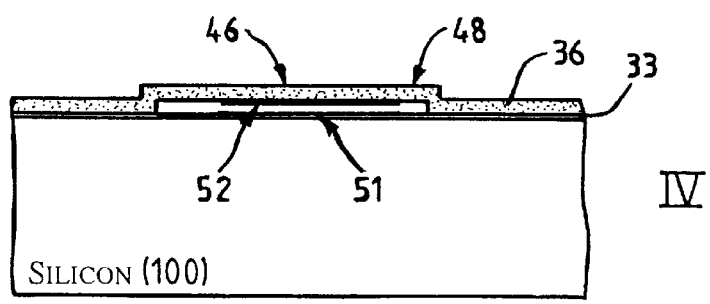
Figure 6E:
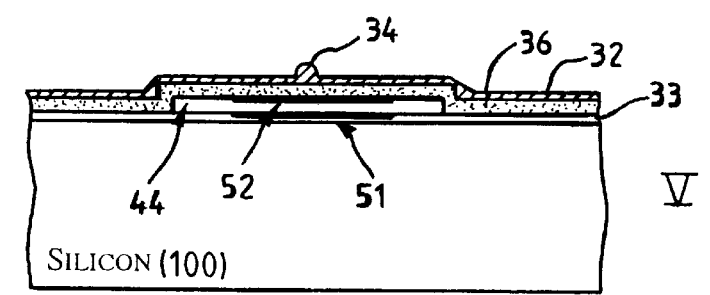

In this exemplary embodiment illustrated in FIGS. 6A–6E, the same references are used to designate the same elements as those in the description of FIGS. 5A–5D.

On a silicon substrate, there is deposited a layer of metal (for example Au or Ti) which will be used either as a first electrode 51 of a variable capacitor or as a first terminal of a microcontactor.

This layer 51 is etched to form the geometry (circular in this embodiment) and the position of the electrode.

An intermediate layer 35 of polycrystalline silicon or a layer of metal such as aluminium (Al) (sacrificed layer) is then deposited. This layer 35 undergoes an operation of photolithographic etching to obtain the (circular) geometry and the position of the diaphragm 46 of the microsensor.

The diaphragm 46 and the electrode 52 are concentric. A second layer of metal 52 (Al or Ti) is deposited to form either the second electrode of the capacitor or the second terminal of the microcontactor. This layer is etched to leave the second electrode in the vertical alignment of the first one.

The second step consists of the deposition of a thin layer of silicon nitride 36 throughout the surface of the substrate.

The third step consists in making a hole on the edge of the diaphragm 36. This hole goes through the layer of nitride to reach the sacrificed layer. Then, a wet etching operation is performed on the substrate. The solution corrodes the sacrificed layer through the hole. The etching continues up to the total disappearance of the sacrificed layer. A cavity is therefore formed. The diaphragm 46 and the upper electrode 52 are completely released.

With the etching being completed, a deposition of silicon nitride 48 is done under vacuum to close the hole and seal the cavity (plug 48).

The final step consists of the deposition of a silicone layer 32 to protect the entire unit and obtain a pad centered in the middle of each microsensor (step V).

What is claimed is:

1. A fingerprint sensor comprising a matrix of pressure microsensors sensitive to the pattern of a fingerprint, the matrix of pressure microsensors being implemented in an integrated circuit, each pressure microsensor of the matrix including a deformable diaphragm which closes off a cavity, the cavity being disposed between the diaphragm and a substrate of the integrated circuit, the diaphragm being formed of an insulator material, and the diaphragm having disposed thereon a conductive element of the microsensor which deforms under the effect of a pressure applied to the diaphragm.

2. A fingerprint sensor according to claim 1, wherein each pressure microsensor comprises a bridge of piezoelectric resistors deposited on a first layer of the insulator material forming the diaphragm, the conductive element disposed on the diaphragm being part of the bridge of piezoelectric resistors, and a resistance of the bridge of piezoelectric resistors providing an indication of the pressure applied to the diaphragm.

3. A fingerprint sensor according to claim 2, wherein the bridge of piezoelectric resistors comprises bands of polycrystalline silicon deposited on the first layer stretched above the cavity.

4. A fingerprint sensor according to claim 3, wherein the cavity is demarcated by walls formed by the first layer, the bridge of piezoelectric resistors lying on the diaphragm suspended above the cavity.

5. A fingerprint sensor according to claim 1, wherein each pressure microsensor comprises a contactor having first and second electrodes which are disposed in the cavity, the first electrode being formed of the conductive element and being fixedly joined to the diaphragm and the second electrode being disposed on the substrate, the contactor being moved between an open position and a closed position based on the pressure applied to the diaphragm, the first and second electrodes being electrically connected to each other in the closed position and being electrically disconnected from each other in the open position.

6. A fingerprint sensor according claim 1, wherein each pressure microsensor comprises a variable capacitor, the variable capacitor having first and second electrodes which are disposed in the cavity, the first electrode being formed of the conductive element and being fixedly joined to the diaphragm, the second electrode being disposed on the substrate, and a capacitance between the first and second electrodes providing an indication of the pressure applied to the diaphragm.

7. A fingerprint sensor according to claim 5, wherein the cavity is demarcated by walls of silicon nitride, a layer of metal lying on the diaphragm suspended above the cavity.

8. A fingerprint sensor according to claim 1, wherein the matrix has at least 128×128 pressure microsensors arranged in an array with a pitch that is smaller than or equal to 65 micrometers.

9. A fingerprint sensor according to claim 1, wherein the pressure microsensors are made on a monolithic substrate and are coated with a layer of flexible material protecting the pressure microsensors and facilitating the transfer of pressure between a finger and the pressure microsensors.

10. A fingerprint sensor according to claim 9, wherein the thickness of the layer of flexible material is increased at the center of each pressure microsensor to form a pad and thus improve the transfer of pressure between the finger and the pressure microsensors.

11. A fingerprint sensor according to claim 1, comprising electronic circuits having means for transmitting, to an output of the fingerprint sensor, electrical signals representing the pressure detected by each pressure microsensor.

12. A fingerprint sensor according to claim 11, wherein the electrical signals representing the pressure detected by each pressure microsensor are binary signals representing whether a threshold of pressure has been exceeded or not exceeded.

13. A fingerprint sensor according to claim 1, wherein the each pressure microsensor has an analog output signal enabling a more precise measurement of the pressure of the finger.

14. A fingerprint sensor comprising:

a matrix of pressure microsensors sensitive to the pattern of a fingerprint, the matrix of pressure microsensors being implemented entirely in an integrated circuit, each pressure microsensor of the matrix including
- a first electrode disposed on a substrate of the integrated circuit,
- a deformable diaphragm which closes off a cavity, the cavity being disposed between the diaphragm and the substrate of the integrated circuit, the diaphragm being formed of an insulator material, and
- a second electrode, the second electrode being disposed on the diaphragm between the diaphragm and the substrate, the second electrode being deformable under the effect of a pressure applied to the diaphragm so as to have an open position and a closed position, the second electrode being electrically connected with the first electrode in the closed position, the second electrode being electrically disconnected from the first electrode in the open position, and the open and closed positions of the second electrode providing an indication of the pressure applied to the diaphragm.

15. A fingerprint sensor comprising:

a matrix of pressure microsensors sensitive to the pattern of a fingerprint, the matrix of pressure microsensors being implemented entirely in an integrated circuit, each pressure microsensor of the matrix including
- a deformable diaphragm which closes off a cavity, the cavity being disposed between the diaphragm and a substrate of the integrated circuit, the diaphragm being formed of an insulator material, and
- a piezoelectric resistor, the piezoelectric resistor being disposed on the diaphragm, the piezoelectric resistor being deformable under the effect of a pressure applied to the diaphragm so as to have a resistance which varies according to the pressure applied to the diaphragm, the resistance providing an indication of the pressure applied to the diaphragm.

16. A fingerprint sensor according to claim 15, wherein the piezoelectric resistor is part of a bridge of piezoelectric resistors, and wherein the bridge of piezoelectric resistors is formed of bands of polycrystalline silicon deposited on a first layer of the insulator material forming the diaphragm.

17. A fingerprint sensor according to claim 16, wherein each pressure microsensor provides an analog output signal.

18. A fingerprint sensor comprising:

a matrix of pressure microsensors sensitive to the pattern of a fingerprint, the matrix of pressure microsensors being implemented entirely in an integrated circuit, each pressure microsensor of the matrix including
- a deformable diaphragm which closes off a cavity, the cavity being disposed between the diaphragm and a substrate of the integrated circuit, the diaphragm being formed of an insulator material, and
- a variable capacitor, the variable capacitor having first and second electrodes which are disposed in the cavity, the first electrode being fixedly joined to the diaphragm, the second electrode being disposed on the substrate, a capacitance between the first and second electrodes providing an indication of the pressure applied to the diaphragm.

19. A fingerprint sensor according to claim 18, wherein each pressure microsensor provides an analog output signal.

* * * * *